(12) United States Patent  (10) Patent No.: US 8,761,488 B2
Kamiyama et al.  (45) Date of Patent: Jun. 24, 2014

(54) IMAGE DATA PROCESSING METHOD AND IMAGE CREATING METHOD

(75) Inventors: Eiji Kamiyama, Tokyo (JP); Shin Uchino, Tokyo (JP)

(73) Assignee: Sumco Corporation, Tokyo (JP)

( * ) Notice: Subject to any disclaimer, the term of this patent is extended or adjusted under 35 U.S.C. 154(b) by 535 days.

(21) Appl. No.: 13/022,062

(22) Filed: Feb. 7, 2011

(65) Prior Publication Data

US 2011/0194753 A1 Aug. 11, 2011

(30) Foreign Application Priority Data

Feb. 8, 2010 (JP) ................................ 2010-025307

(51) Int. Cl.
  *G06K 9/00*  (2006.01)
(52) U.S. Cl.
  USPC ........................................................ 382/145
(58) Field of Classification Search
  None
  See application file for complete search history.

(56) References Cited

U.S. PATENT DOCUMENTS

| | | | |
|---|---|---|---|
| 6,529,270 B1 | 3/2003 | Bills | |
| 6,552,337 B1 * | 4/2003 | Cho et al. | 850/33 |
| 7,151,858 B2 * | 12/2006 | Kyong | 382/266 |
| 7,346,883 B2 * | 3/2008 | Keck et al. | 700/121 |
| 7,528,944 B2 * | 5/2009 | Chen et al. | 356/237.6 |
| 8,379,196 B2 * | 2/2013 | Kamiyama et al. | 356/237.2 |
| 2004/0080741 A1 | 4/2004 | Marxer et al. | |
| 2009/0037134 A1 * | 2/2009 | Kulkarni et al. | 702/127 |
| 2009/0279081 A1 | 11/2009 | Urano | |

FOREIGN PATENT DOCUMENTS

JP 2001083080 A 3/2001

OTHER PUBLICATIONS

Single image haze removal using dark channel paior, by He et. al. IEEE 978-1-4244-3991-1/2009; pp. 1956-1963.*
"Optical Scattering Measurement and Analysis"; Optical and Electra-Optical Engineering Series, John C. Stover, pp. 45-65, 1990.

* cited by examiner

*Primary Examiner* — Vikkram Bali
(74) *Attorney, Agent, or Firm* — Thomas J. Engellenner; Reza Mollaaghababa; Pepper Hamilton LLP

(57) ABSTRACT

[Problem] Provided is a method of processing image data capable of, at the time of measuring a wafer in a circumferential direction thereof using a surface inspection device employing a laser scattering method to create a Haze map, reducing or removing occurrence of a noise resulting from change in detection sensitivity of the device. Further, provided is a method of creating an image by using the method of processing an image data.

[Solving Means] There is provided a method of processing image data, including the steps of: measuring a haze value corresponding to each position on a wafer surface by using a wafer surface inspection device; and, subjecting image data formed by the haze value corresponding to each position on the wafer surface to an image data process along a direction in which the haze value is measured, to remove a noise component. Further, there is provided a method of creating an image, in which a Haze map after the image data process is created using the image data processed through the method of processing the image data.

3 Claims, 8 Drawing Sheets

(a)

(b)

(c)

(a)

(b)

(a)

(b)

(c)

IMAGE DATA PROCESSING METHOD AND IMAGE CREATING METHOD

TECHNICAL FIELD

The present invention relates to a method of processing image data and image creating method, and in particular, to a method of processing image data obtained at the time of inspecting a wafer surface using a scattered light occurring at the time when the wafer surface is irradiated with a laser light, and a method of creating an image by using said method of processing image data.

RELATED ART

In general, it is well known that particles or defects on a surface of a semiconductor wafer before formation of a device pattern largely affect quality of a semiconductor device produced using said semiconductor wafer. Therefore, conventionally, a surface of a semiconductor wafer produced is inspected through an inspection method using scattering a laser (laser scattering method) at the time of producing and shipping the semiconductor wafer, and the number of particles or surface defects, which are detected as light point defects (LPDs), is measured, so that quality of the produced semiconductor wafer can be evaluated. More specifically, by using the detected number of LPDs as a reference, an evaluation is made as to whether the produced semiconductor wafer is a non-defective item or defective item.

As a surface inspection device that employs the laser scattering method, there is known a surface inspection device having a laser light source for irradiating a wafer surface with a laser beam from above a wafer, a condensing lens or mirror (condensing plate) for condensing scattered lights generated at the time of irradiation of the wafer surface with the laser light, a photoelectric conversion element for converting the condensed scattered light into an electric signal for detection (see, for example, US Patent Application laid open No. 2004/0080741). With this surface inspection device, the photoelectric conversion element detects both a scattered light resulting from particles and defects on the wafer surface, and a scattered light assumed to be generated due to microroughness and the like on the wafer surface (see, for example, "Optical Scattering: Measurement and Analysis", John C. St over, McGraw-Hill, 1990) at the time of irradiation of the wafer surface with the laser light.

In recent years, with the shrinking of the size of semiconductor devices (finer and smaller), such semiconductor wafers are required to be further high quality. For this reason, in the field of quality evaluation of the semiconductor wafers, further smaller particles and surface defects having, for example, a size of 40 nm or lower are required to be detected.

However, as described above, with the surface inspection device employing the laser scattering method, the photoelectric conversion element detects the scattered light resulting from the microroughness and the like on the wafer surface, in addition to the scattered light resulting from the particles and defects on the wafer surface. Further, in general, as the intensity of the scattered light resulting from the micro-particles and surface defects is relatively low, it was difficult for the conventional surface inspection device to, at the time of detection, clearly separate a signal resulting from the micro-particles and surface defects and a detected signal resulting from the microroughness and the like on the wafer surface (haze signal: background signal obtained by removing the LPD signal from the detected signals using band-pass filter and the like) from among detected signals resulting from the particles and defects on the wafer surface (LPD signal). Therefore, with the method of evaluating the semiconductor wafer using the conventional surface inspection device, there occurred a case where the LPD signal is buried in the haze signal and cannot be detected or a case where the haze signal is detected as the LPD signal. Accordingly, the semiconductor wafer cannot be evaluated accurately, possibly causing various troubles and increasing the production cost.

DISCLOSURE OF THE INVENTION

Problems to be Solved by the Invention

As a method of accurately evaluating the quality of the semiconductor wafer taking such a problem into consideration, there is a method of evaluating the semiconductor wafer, including: from among signals detected by the surface inspection device, taking a signal having an intensity of a certain level of threshold value or more as the LPD signal; taking a baseline portion of a signal having an intensity of less than the threshold value as the haze signal; creating a LPD map based on the LPD signal and a Haze map based on the haze signal; thereby evaluating the semiconductor wafer. More specifically, this method evaluates the quality of the semiconductor wafer such that: the LPD map and the Haze map are created by using the signals (LPD signal and haze signal) detected by the surface inspection device as image data; from the created Haze map, a haze singular point is extracted using a predetermined method; and, the LPD detected in the LPD map and the haze singular point detected in the Haze map are taken as the total defective points existing on the wafer surface.

In general, in order to efficiently measure a disk-shaped wafer, the conventional surface inspection device measures the LPD and the like, for example, in a spiral manner in a direction from the center C of the wafer toward the outer circumference, or in a direction from the outer circumference toward the center C as illustrated in FIGS. 2(a) and 2(b), by rotating and moving the wafer while a position of a laser light source remains fixed. This is because, in a case where the wafer surface is measured in the X-Y direction by making the wafer reciprocate in the linear direction while the position of the laser light source remains fixed, it is necessary to reverse the measurement direction at the end of the wafer, which requires the traveling speed of the wafer to be reduced at the turning point, taking longer time for measurement. On the other hand, in a case of the measurement with the spiral form, it is possible to rapidly measure the wafer surface at a constant speed without reducing the speed.

Generally, in the surface inspection device, the detection sensitivity is changed slightly during the measurement (change with time) due to physical change in the device environment.

Accordingly, in a case where the surface inspection device measures the surface of the wafer in the spiral manner, a difference in detection sensitivity of the surface inspection device between the measurement positions adjacent to each other in the radial direction of the wafer surface tends to be larger than a difference in detection sensitivity of the surface inspection device between the measurement positions adjacent to each other in the measurement direction (circumferential direction on the concentric circle).

Therefore, in a case where the wafer surface is measured by using the conventional surface inspection device and the obtained signal is utilized as image data to create an image (Haze map and the like), there existed a case were circular-shaped noises occur resulting from change in the detection sensitivity during measurement (see, for example, FIG. 6).

The occurrence of such noises makes it difficult to accurately detect the haze singular point, and has been an extremely large problem in terms of evaluation of the quality of the wafer using the Haze map. This is because, in a case where the wafer surface after polishing is measured using a surface inspection device (SP2) made by KLA-Tencor for example, an average value of values of the haze signal (haze value) of the surface is 0.200 ppm or lower, and distribution of haze values of the surface is 0.200 ppm or lower (0.050 ppm or lower in a case of non-defective unit). Thus, the level of the noises (about 0.001 ppm) resulting from the change in detection sensitivity with time cannot be ignored with respect to the haze value, preventing the accurate Haze map from being obtained.

As a result, there has been a demand for an image data processing method capable of reducing or removing occurrence of circular-shaped noises (noises along the measurement direction) resulting from the change in the detection sensitivity of the surface inspection device employing the laser scattering method at the time of measuring the wafer in the circumferential direction thereof by using the surface inspection device to create a Haze map. Further, there is also a demand for a method of creating an image (Haze map that has been subjected to image data processing) by using said image data processing method.

Means for Solving the Problem

An object of the present invention is to advantageously solve the problem described above, and according to the present invention, there is provided a method of processing image data, which includes the steps of: measuring a haze value corresponding to each position on a wafer surface by using a wafer surface inspection device that irradiates a surface of a wafer with a laser light while the wafer is being rotated around a center of the wafer, and converts a light scattering on the wafer surface into an electric signal to implement detection; and, subjecting image data formed by a haze value corresponding to each position on the wafer surface to an image data process along a direction in which the haze value is measured to remove a noise component. In a case where the wafer is measured in the circumferential direction by using the surface inspection device as described above, it is possible to reduce or remove the circular-shaped noise resulting from change in the detection sensitivity of the device, by subjecting collection (image data) of the haze value at each position on the wafer surface to the image data process along the direction in which the haze value is measured.

It should be noted that, in the present invention, the expression "subjecting image data to a image data process along a direction in which the haze value is measured" means, for example, that the image data process is performed in a direction along a curvature of the spiral form when a position on the wafer to be irradiated with the laser light is moved in a spiral form by moving the wafer in one direction while rotating the wafer in a state where a position of a light source of a laser light with which the wafer is irradiated remains fixed (see FIGS. 2(a) and 2(b)), and, the image data process is performed in a direction along the circumferential direction on the concentric circle when a position on the wafer to be irradiated with the laser light is moved in a concentric manner (see FIG. 2(c)).

The method of processing image data according to the present invention preferably includes, at the time of subjecting the image data to the image data process, the step of calculating a difference between a haze value at a given position of the wafer surface and an average value of haze values at two or more positions adjacent to the given position along the direction in which the haze value is measured, to remove a noise component at the given position. This is because it is possible to easily remove the noise component in the circumferential direction, by calculating, for each position on the wafer surface, the difference between a haze value at a position to be processed and an average value of haze values at two or more positions adjacent to the position to be processed along the direction in which the haze value is measured, and using the obtained value as image data after the process at the processing-target position. It should be noted that, in the present invention, the expression "adjacent along a direction in which a haze value is measured" includes a case where positions are adjacent to each other in the direction same as a direction in which the haze value is measured and a case where positions are adjacent to each other in a direction opposite to the direction in which the haze value is measured.

Further, the method of processing image data according to the present invention preferably includes the steps of: subjecting image data formed by a haze value corresponding to each position on the wafer surface to an image data filtering process in a X-Y direction to obtain first image data; and, combining the first image data with second image data obtained by removing the noise through the step of subjecting the image data to the image data process, in order to obtain third image data. This is because it is possible to further reliably remove the noise component in the circumferential direction and reduce or remove the noise component in the X-Y direction, by combining the first image data obtained by subjecting the collection (image data) of haze values corresponding to each position on the wafer surface to an image data filtering process in a X-Y direction with the second image data obtained by subjecting the image data same as the image data subjected to the image data filtering process in a X-Y direction to image data process along the direction in which the haze value is measured.

Yet further, an image creating method according to the present invention is characterized in that a Haze map after the image data process is created by using the image data processed through the method of processing image data described above. This is because, by creating the image (Haze map after the image data process) using the image data obtained through the process according to the image data processing method described above, from which image data the circular-shaped noise is reduced or removed as described above, the noise component is removed from the Haze map, whereby it is possible to accurately extract a characteristic portion (haze singular point and the like) from the Haze map after the image data process.

Effect of the Invention

According to the method of processing image data of the present invention, it is possible to, at the time of measuring a wafer in a circumferential direction by using a surface inspection device employing a laser scattering method to create a Haze map, reduce or remove occurrence of a circular-shaped noise resulting from change in detection sensitivity of the device. Further, according to an image creating method of the present invention, it is possible to create an accurate Haze map from which a circular-shaped noise is reduced or removed.

BEST MODE FOR CARRYING OUT THE INVENTION

Figure 1:
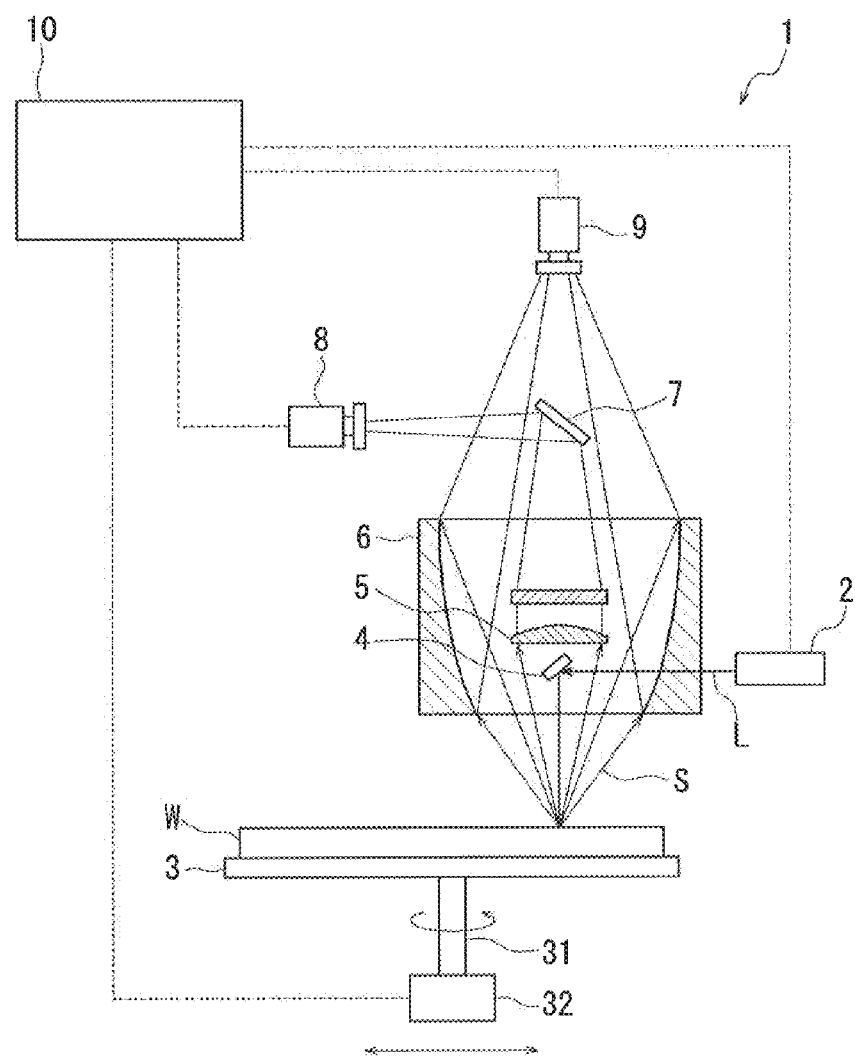
FIG. 1 is an explanatory diagram illustrating an example of a configuration of a surface inspection device for use in implementing a method of processing image data and a method of creating an image according to the present invention.

Hereinbelow, an embodiment according to the present invention will be described with reference to the drawings. FIG. 1 is an explanatory diagram illustrating an example of a configuration of a surface inspection device for use in implementing a method of processing image data and a method of creating an image according to the present invention.

A surface inspection device 1 illustrated in FIG. 1 employs a laser scattering method, in which a surface of a wafer W is scanned with a laser light L, and a scattered light S from the wafer surface is detected as a LPD signal or haze signal.

The surface inspection device 1 includes: a laser light source 2; a supporting stage 3 on which the wafer W is placed; a first reflecting plate 4 provided above the supporting stage 3, which reflects the laser light L outputted from the laser light source 2 and guides the reflected laser light L to the wafer W placed on the supporting stage 3; a condensing lens 5 and a condensing plate 6 that converge the scattered light S from the wafer surface; a second reflecting plate 7 that reflects the scattered light S converged by the condensing lens 5 and guides the reflected light S to a first detector (photomultiplier) 8; a second detector (photomultiplier) 9 that detects the scattered light S converged by the condensing plate 6; and, a control unit 10. Note that the supporting stage 3 of the surface inspection device 1 is supported by a rotation and movement shaft 31, and the supporting stage 3 and the rotation and movement shaft 31 are configured so as to be able to move in the right and left direction in FIG. 1 while rotating, by a driving unit 32 provided below the rotation and movement shaft 31. Further, the control unit 10 is electrically connected with the laser light source 2, the driving unit 32, the first detector 8 and the second detector 9.

Figure 2:
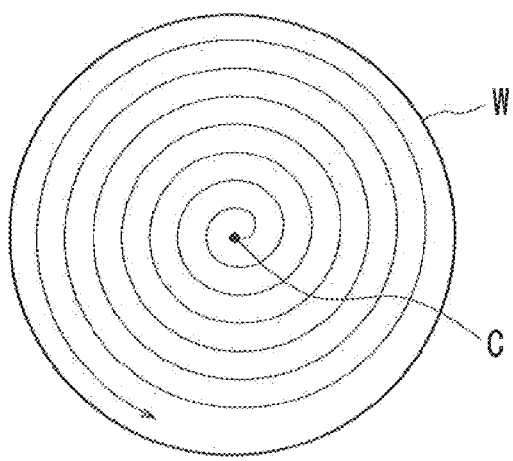
FIGS. 2(a) through 2(c) are explanatory diagrams each illustrating a direction in which a haze value is measured by using the surface inspection device.
Figure 2:
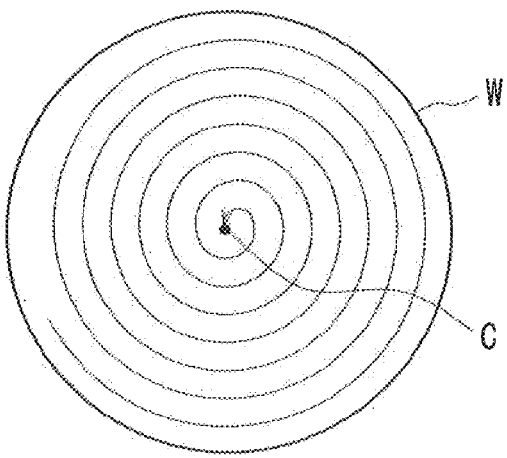
Figure 2:
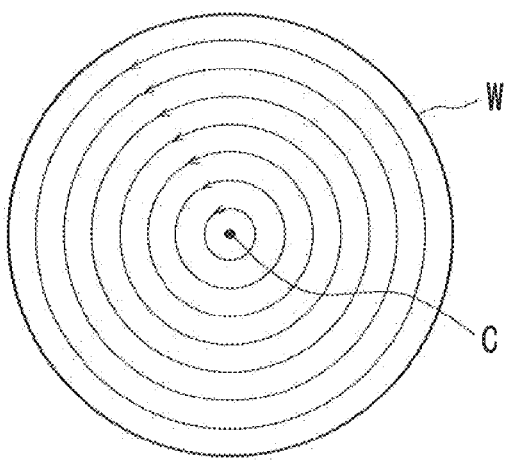

In the surface inspection device 1, the surface of the wafer W placed on the supporting stage 3 is irradiated with the laser light L from the laser light source 2 through the first reflecting plate 4 while the wafer W is being rotated and moved together with the supporting stage 3 around the center of the wafer W. At this time, the rotation and movement of the supporting stage 3 and the wafer W may be performed such that the surface of the wafer W is scanned with the laser light L in a spiral form from the center C of the wafer toward the outer circumference of the wafer as illustrated in FIG. 2(a), or may be performed such that the surface of the wafer W is scanned with the laser light L in a spiral form from the outer circumference of the wafer toward the center C of the wafer as illustrated in FIG. 2(b), or may be performed such that the surface of the wafer W is scanned with the laser light L in a concentric manner as illustrated in FIG. 2(c).

Further, in the surface inspection device 1, the scattered light S from the surface of the wafer W is detected by the first detector 8 and the second detector 9 and is converted into an electric signal, thereby to obtain a LPD signal based on a scattered light resulting from particles or defects on the wafer surface, and a haze signal obtained by removing the LPD signal from the signal of the total detected scattered light by using the band-pass filter and the like. More specifically, in the surface inspection device 1, positional information of the wafer surface irradiated with the laser light L, which can be known from the amount of rotation and movement of the driving unit 32, and the LPD signal and the haze signal detected by the first detector 8 and the second detector 9 are sent to the control unit 10, thereby detecting the LPD signal and the haze signal corresponding to each position on the wafer surface.

In an example of an image data processing method according to the present invention, the process described below for example is performed to a Haze map before the image data process, the Haze map being obtained by color coding the magnitude of the haze signal (haze value) corresponding to each position on the wafer surface and detected by the first detector 8 of the surface inspection device 1 in a 256-level gray scale in accordance with the magnitude of the value of the haze signal, thereby to create an image. Note that the process of the haze value may be performed, for example, by a hardware resource (not illustrated) such as a computer. Further, it may be possible to perform the process of the haze value directly to a haze value corresponding to each position on the wafer surface, without creating the Haze map before the image data process.

In a direction along a direction in which the haze values are measured (i.e. laser-light scanning direction), an image data process is performed to an original image data formed by a collection of haze values corresponding to the respective positions on the wafer surface (Haze map before image data process in this example) to remove the noise component, whereby it is possible to obtain image data from which noises are removed (noise-removing process).

As described above, according to the example of the image data processing method of the present invention, it is possible to reduce or remove the noise component in the circumferential direction (measurement direction) resulting from change in detection sensitivity of the device through the noise-removing process, in a case where the haze values of the wafer are measured in the circumferential direction by the surface inspection device.

It should be noted that, in the image data processing method according to the present invention, a third image data may be obtained by combining a first image data obtained by subjecting the original image data to a filtering process in a X-Y direction, and a second image data obtained by removing the noise component through the noise-removing process.

As described above, it is possible to further reliably remove the noise component in the circumferential direction while reducing or removing the noise component in the X-Y direction, by combining the first image data obtained by subjecting the original image data to the filtering process in a X-Y direction, and a second image data obtained by performing the image data process along the direction in which the haze values are measured. Note that the combination of the first image data and the second image data can be made by obtaining a sum or product of values of pixels at the same position on the wafer in the first image data and the second image data, or other known methods.

Figure 3:
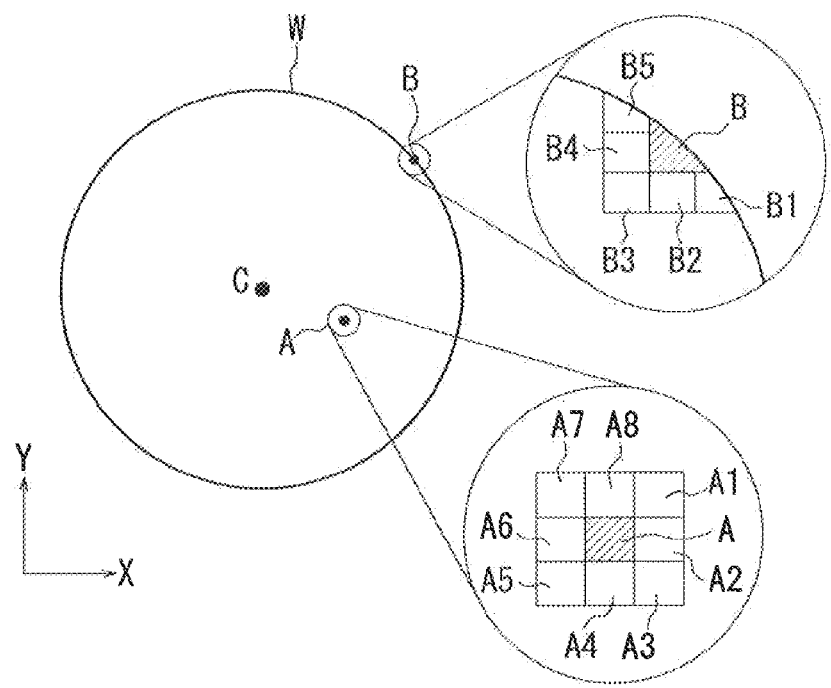
FIGS. 3(a) and 3(b) are diagrams for explaining a method of processing image data at the time when the image data is processed in accordance with the method of processing image data according to the present invention.
Figure 3:
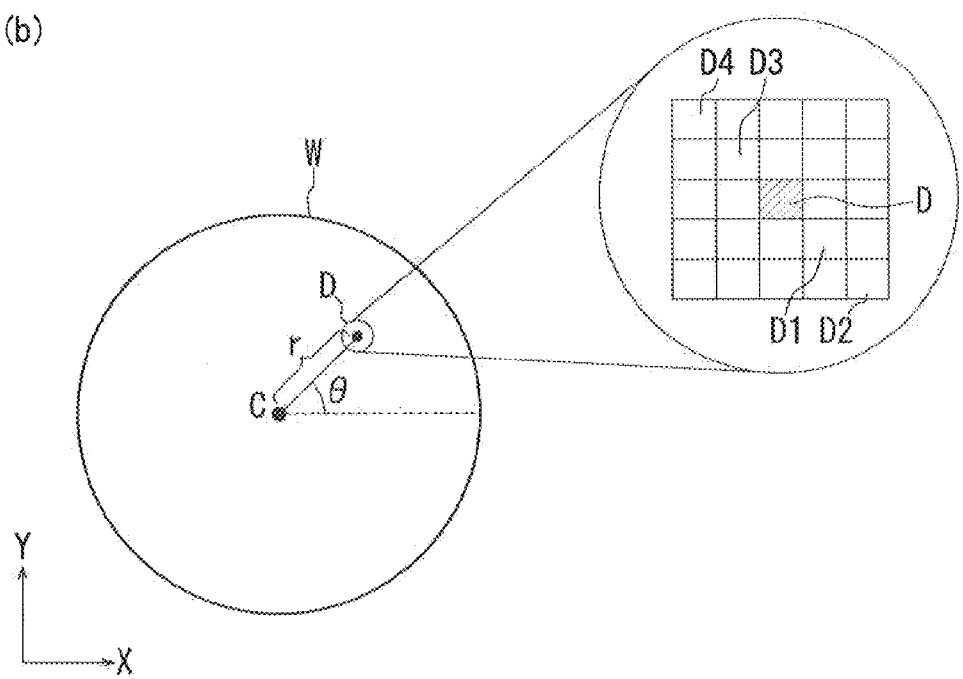

The filtering process in the X-Y direction (image data filtering process) can be performed, for example, by using a haze value at a position to be subjected to the filtering process and a haze value in the vicinity of the position to be subjected to the filtering process. More specifically, for example, in a case where a haze value of a point A on the wafer W illustrated in FIG. 3(a) is subjected to the filtering process, haze values of eight points (A1 through A8) adjacent to the point A are used as shown in an enlarged view in FIG. 3(a); an average value of haze values of the total nine points including the point A and the points A1 through A8 is subtracted from the haze value on the point A; and the obtained value is used as a value of a pixel located at the point A in the image data after the filtering process. Further, in a case where a haze value of a point B on the wafer W illustrated in FIG. 3(a) is subjected to the filtering process, haze values of five points (B1 through B5) adjacent to the point B are used as shown in an enlarged view in FIG. 3(a); an average value of haze values of the total six points including the point B and the points B1 through B5 is subtracted from the haze value on the point B; and, the obtained value is used as a value of a pixel located at the point B in the image data after the filtering process. Note that the number of points of haze values used for the filtering process may be varied depending on application. More specifically, it may be possible to perform the filtering process by using an average value of the point A, eight points adjacent to the point A and 16 points located on the outer periphery of said eight points (24 points in total). This makes it possible to lengthen a cutoff (space) wavelength of the noise component to be removed by the filtering process in the X-Y direction, whereby it is possible to create a smoother image having reduced effect of the noise component. Further, the filtering processing method is not limited to the method of subtracting the average value as described above, and other known methods may be applied depending on application.

The noise component can be removed by using a haze value at a position to be subjected to the noise component removing process, and haze values located at adjacent two points along the direction in which the haze value is measured (the laser-light scanning direction). More specifically, for example, in a case where a noise component at a position of a point D (a point represented by polar coordinate (r, θ)) on the wafer W illustrated in FIG. 3(b) is removed, haze values of four points in total (D1 through D4) located adjacent to the point D along the circumferential direction are used as shown in an enlarged view in FIG. 3(b), and it is possible to use a value obtained by subtracting an average value of haze values of the total five points including the point D and the points D1 through D4 from the haze value on the point D, as a value of a pixel located at the point D in the image data after removal of the noise component, whereby the noise component at the point D can be removed. Note that the number of points of haze values used for the removal of the noise component may be varied depending on application, and for example, it is possible to use two or more points located on the same circle having a radius r along the direction in which the haze values are measured. Although the detection sensitivity of the surface inspection device changes during the time when the scanning point makes a circuit of the wafer, it is possible to effectively remove the noise resulting from the change in the detection sensitivity of the surface inspection device, by removing the noise component by using the points located on the same circle. Note that the number of haze values used for the removal of the noise component may be varied depending on application, similar to the case of the filtering process in the X-Y direction described above. Further, the method of removing the noise component is not limited to the method described above, and known methods may be applied depending on application.

It should be noted that the method of processing image data according to the present invention described above can be suitably applied to a wafer particularly requiring quality evaluation using the Haze map, for example, a wafer requiring detection of LPD having a size of 35 nm or lower (inspection of LPD whose minimum size is 35 nm or lower). This is because, in a case of inspection of LPD whose minimum size is 35 nm or lower, it is necessary to further lower the threshold value between the LPD signal and the haze signal in order to detect a feeble LPD signal as a defect, which also decreases a haze value of the wafer detected by the surface inspection device; and hence, it is particularly desired to establish the method capable of obtaining further accurate Haze maps.

Further, in an example of an image creating method according to the present invention, it is possible to create a Haze map (Haze map after image data process) from which the noise component in the circumferential direction is removed, by using the image data processed in accordance with the method of processing the image data according to the present invention described above, and color-coding each position on the wafer in a 256-level gray scale in accordance with a magnitude of a haze value at the position.

EXAMPLE

Example 1

A haze value of the wafer after polishing was measured by using a surface inspection device (SP2 made by KLA-Tencor). Note that the measurement of the haze value was made in a spiral form.

Figure 4:
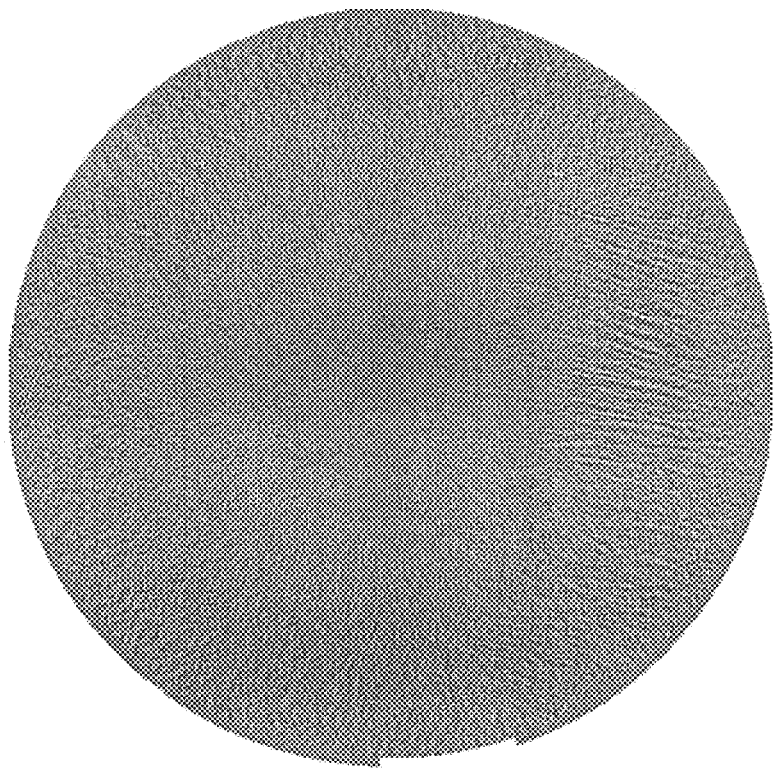
FIG. 4 is an image of a laze map after the image data process according to Example.

Further, for original image data obtained by the surface inspection device, the noise removal process was performed, and, the image data after the noise removal process were converted into a map in a 256-level gray scale, thereby to create a Haze map. The created Haze map is illustrated in FIG. 4.

It should be noted that, in the noise removal process, from a haze value at a position to be processed, an average value of haze values at six points adjacent along the direction in which the haze value is measured (three points in a direction in which the haze value is measured, and three points in a direction opposite to the direction in which the haze value is measured) is subtracted, and the obtained value is used as a value of a pixel located at the position to be processed in the image data after the removal of the noise.

Example 2

Figure 5:
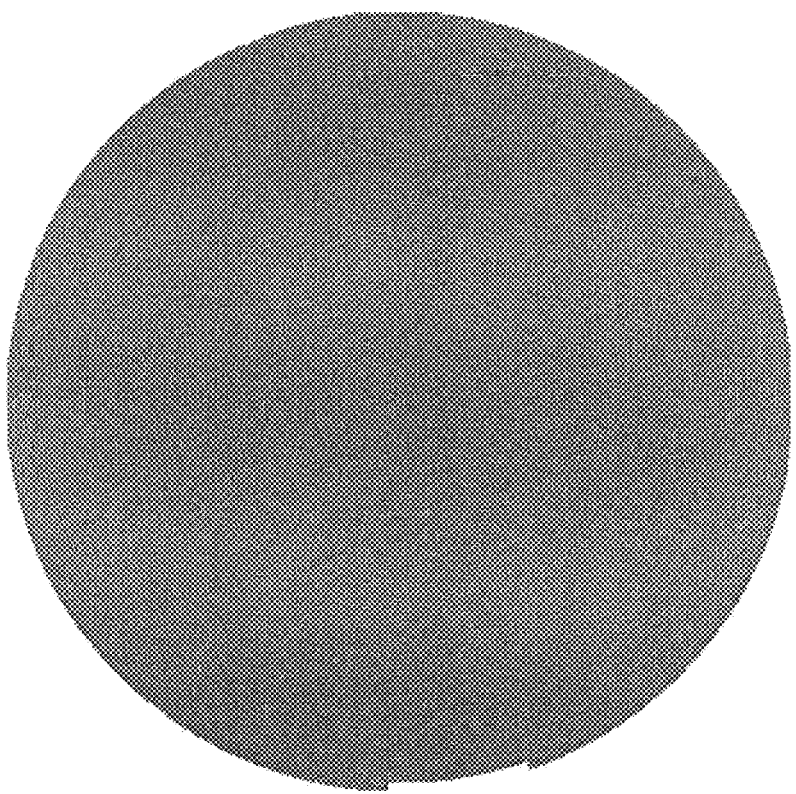
FIG. 5 is an image of a Haze map after the image data process according to Example.

The image data obtained by subjecting the original image data obtained in Example 1 to the filtering process, and the image data obtained by applying the noise removal process in Example 1 were combined, and thus obtained image data was subjected to a mapping process in a 256-level gray scale, thereby to create a Haze map. The created Haze map is illustrated in FIG. 5.

It should be noted that, in the filtering process, from a haze value at a position to be subjected to the filtering process, an average value of the haze value at the position to be subjected to the filtering process and haze values at eight points adjacent thereto is subtracted, and the obtained value is used as a value of a pixel at the position to be processed in the image data after the filtering process. Further, the combination is made by obtaining a sum of values of the pixel located at the same position on the wafer in the respective image data, and using the obtained value as a value of pixel in the image data after the combination at the positional.

Conventional Example 1

Figure 6:
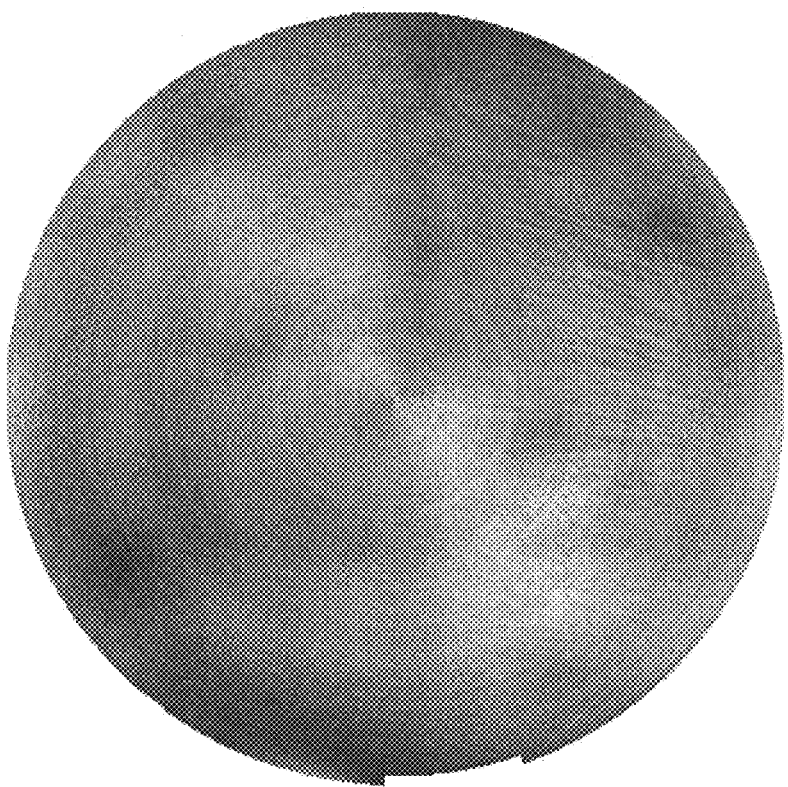
FIG. 6 is an image of a Haze map according to Conventional Example.

The original image data obtained in Example 1 was subjected to a mapping process in a 256-level gray scale, thereby to create a Haze map. The created Haze map is illustrated in FIG. 6.

Comparative Example 1

The original image data obtained in Example 1 was subjected to a filtering process similar to Example 2. Then, the image data after the process was subjected to a mapping process in a 256-level gray scale, thereby to create a Haze map. The created Haze map was illustrated in FIG. 7.

Experimental Example

Measurement of a haze value was made three times on the same polished wafer by using a surface inspection device (SP2 made by KLA-Tencor). Then, the obtained three types of original image data were subjected to a mapping process in a 256-level gray scale, and three Haze maps were created. The created Haze maps are illustrated in FIGS. 8(a) through 8(c).

Figure 8:
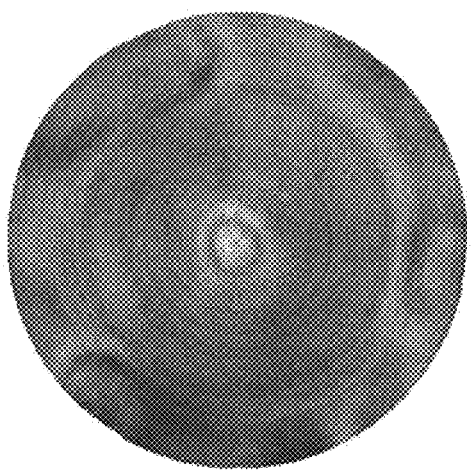
FIGS. 8(a) through 8(c) are images of Haze maps having different occurrence patterns of a circular-shaped noise obtained in a case where the same wafer is measured three times by the surface inspection device.
Figure 8:
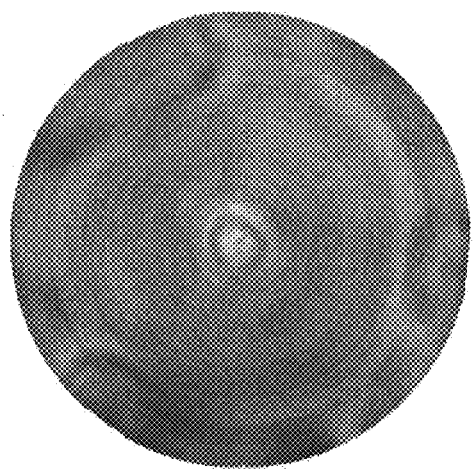
Figure 8:
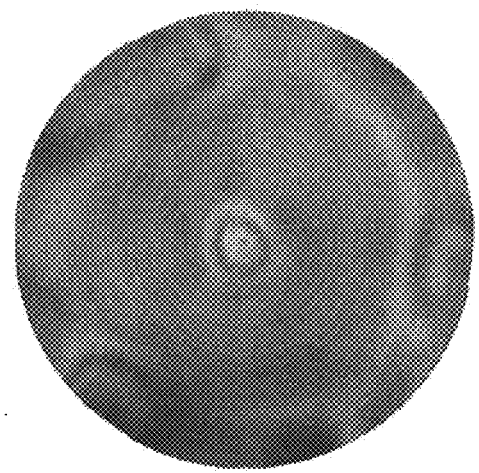

In FIGS. 8(a) through 8(c), circular-shaped trajectories appearing on the Haze maps are changed, and hence, it can be understood that circular-shaped noises occur in the Haze maps created from the original image data.

Figure 7:
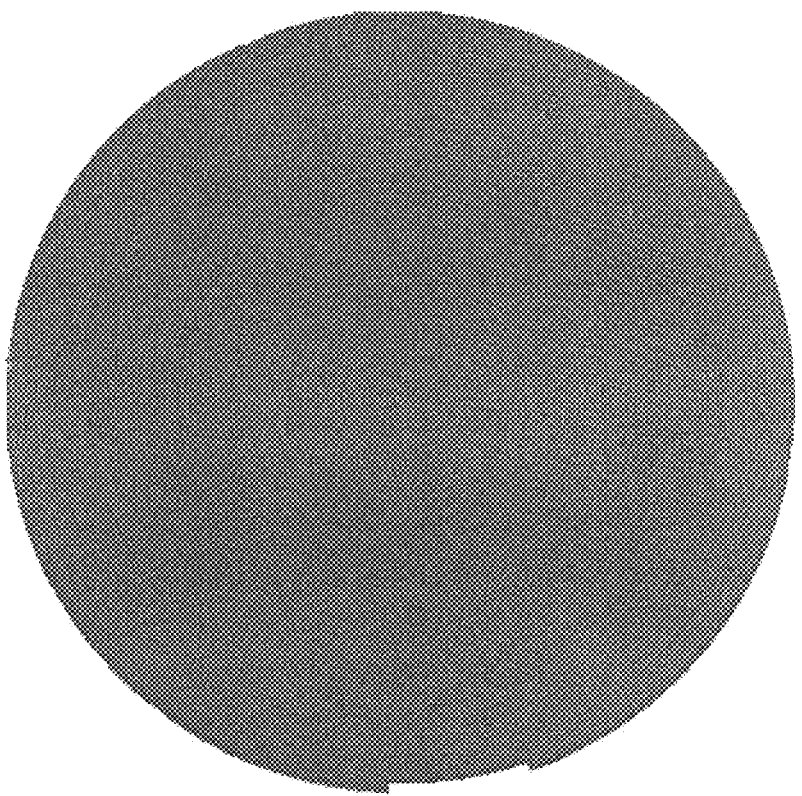
FIG. 7 is an image of a Haze map after the image data process according to Comparative Example.

On the other hand, in FIGS. 4 and 5, no circular-shaped trajectories, which appear in FIGS. 6 and 7, can be seen, and hence, it can be understood that, according to the image data processing method of the present invention, the circular-shaped noises are reduced or removed and accurate Haze map can be created.

INDUSTRIAL APPLICABILITY

According to an image data processing method of the present invention, at the time of measuring a wafer in a circumferential direction by using a surface inspection device employing a laser scattering method and creating a Haze map, it is possible to reduce or remove occurrence of a circular-shaped noise resulting from change in detection sensitivity of the device. Further, according to an image creating method of the present invention, it is possible to create an accurate Haze map from which a circular-shaped noise is reduced or removed.

The invention claimed is:

1. A method of processing image data, comprising the steps of:
    measuring a haze value corresponding to each position on a wafer surface by using a wafer surface inspection device that irradiates a surface of a wafer with a laser light while the wafer is being rotated around a center of the wafer, and converts a light scattered on the wafer surface into an electric signal to implement detection;
    subjecting image data formed by the haze value corresponding to each position on the wafer surface to an image data filtering process in a X-Y direction to obtain first image data;
    subjecting image data formed by the haze value corresponding to each position on the wafer surface to an image data process along a direction in which the haze value is measured to remove a noise component to obtain second image data; and
    combining the first image data with the second image data to obtain third image data.

2. The method of processing image data according to claim 1, further comprising the step of,
    at the time of subjecting the image data to the image data process, calculating a difference between a haze value at a given position on the wafer surface and an average value of haze values at two or more positions adjacent to the given position along the direction in which the haze value is measured, to remove a noise component at the given position.

3. An image creating method, wherein
    a Haze map after the image data process is created by using the image data processed through the method of processing image data according to any one of claims 1 and 2.

* * * * *